United States Patent
Chung et al.

(10) Patent No.: US 7,175,661 B1
(45) Date of Patent: Feb. 13, 2007

(54) APPARATUS AND METHOD FOR IMPROVING VISION UTILIZING A CORNEA-SUPPORTED ARTIFICIAL INTRAOCULAR LENS

(75) Inventors: Young Taek Chung, 109-206, Sangsang Town, Hyoja-dong, Wansan-ku, Chonju, Chonbuk (KR); Mu Suk Lee, Seoul (KR); Byung Ki Ahn, Seoul (KR)

(73) Assignee: Young Taek Chung, Chonbuk (KR)

( * ) Notice: Subject to any disclaimer, the term of this patent is extended or adjusted under 35 U.S.C. 154(b) by 743 days.

(21) Appl. No.: 10/306,099

(22) Filed: Nov. 27, 2002

Related U.S. Application Data

(63) Continuation-in-part of application No. 09/860,234, filed on May 18, 2001, now abandoned.

(30) Foreign Application Priority Data

Jun. 9, 2000 (KR) ......................................... 2001-31581

(51) Int. Cl.
*A61F 2/16* (2006.01)

(52) U.S. Cl. .................... 623/6.41; 623/6.43; 623/6.46
(58) Field of Classification Search ............... 623/6.11, 623/6.41, 6.43, 6.46
See application file for complete search history.

(56) References Cited

U.S. PATENT DOCUMENTS

| 4,451,938 A | * | 6/1984 | Kelman | 623/6.19 |
| 6,342,058 B1 | * | 1/2002 | Portney | 606/107 |
| 6,478,821 B1 | * | 11/2002 | Laguette et al. | 623/6.49 |
| 6,482,229 B1 | * | 11/2002 | Gwon et al. | 623/6.43 |

* cited by examiner

*Primary Examiner*—Corrine McDermott
*Assistant Examiner*—Hieu Phan
(74) *Attorney, Agent, or Firm*—Harrison & Egbert

(57) ABSTRACT

An apparatus for improving vision including an intraocular lens, haptics extending outwardly from a periphery of the intraocular lens, a first anchor connected to the haptics and a second anchor connected to the haptics so as to position the intraocular lens in the anterior chamber of a cornea. Each of the first and second anchors is implanted into the cornea or into the sclera adjacent to the cornea. The intraocular lens has a truncated circular shape.

14 Claims, 4 Drawing Sheets

APPARATUS AND METHOD FOR IMPROVING VISION UTILIZING A CORNEA-SUPPORTED ARTIFICIAL INTRAOCULAR LENS

RELATED U.S. APPLICATIONS

The present application is a continuation-in-part of U.S. patent application Ser. No. 09/860,234, filed on May 18, 2001, and entitled "CORNEA-SUPPORTED ARTIFICIAL INTRAOCULAR LENS", now abandoned.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to an artificial intraocular lens attachable to the cornea. More particularly, the present invention relates to a method and apparatus for installing such an intraocular lens within the anterior chamber of the cornea by implanting anchor members into the cornea or the sclera adjacent to the cornea.

BACKGROUND OF THE INVENTION

In order to better understand the background of the present invention, a description will be given of the eye in conjunction with the FIG. 1. With reference to FIG. 1, there is shown the anatomy of the eye in a cross-sectional view. In the eye, incident light beams are refracted mainly in a cornea 1 and lens 5 so as to form a focus on a retina 9, as in a camera. This allows a human to visualize or see an image or a scene from the retina 9 as transmitted by the optic nerve 8. When becoming turbid for congenital or acquired reasons, the lens 5 cannot refract external light beams appropriately to form a focused image on the retina 9. Serious turbidity of the lens 5 may result in the loss of one's sight.

As shown in FIG. 1, an anterior chamber 2 is formed behind the forward portion of the cornea 1 and ahead of the iris plane 3 and forward of the forward surface 4 of the crystalline lens 5. Sclera 7 extends outwardly from the cornea 1 along the eye. Vitreous body 6 will reside behind the lens 5 and forward of the retina 9. The vitreous body will fill the interior of the eyeball. A posterior chamber 10 is positioned rearwardly of the anterior chamber 2 so as to communicate the fluid flow of aqueous humor between the posterior chamber and the anterior chamber.

When the lens is turbid to such a serious extent as to cause blindness, it is replaced with an artificial lens to recover the sight. In this regard, surgical insertion of an artificial lens in the eyeball is well known. For example, the anterior chamber angle, the ciliary body, or the capsular lentis is the place where an artificial lens is inserted. In addition, an artificial lens may be supported on the iris 3.

However, some of these tissues, e.g. the iris, are anatomically so unstable that an artificial lens cannot be fixed thereto. For example, if an artificial lens is surgically transplanted to be supported by the iris, the patient may suffer from a complication. In addition, because the conventional sites in which an artificial lens is inserted are distant from the cornea, in which the greatest refraction of incident beams occurs, the actual refraction after the operation often does not agree with expected refraction.

In the past, various U.S. patents have issued relating to such intraocular lenses. For example, U.S. Pat. No. 4,950,288, issued on Aug. 21, 1990 to C. D. Kelman, describes a corrective intraocular lens which is inserted through an incision into the eye and implanted therein in spaced relationship to the natural lens. This intraocular lens includes a lens body having a pair of opposed haptics including a first insertable leading haptic and a last insertable trailing haptic. Each haptic outwardly terminates in a transverse edge having a pair of laterally spaced-apart and outwardly projecting contact lobes for engaging an adjacent eye tissue portion at a corresponding pair of spaced-apart tissue points. Unfortunately, this type of intraocular lens rotates relatively easily in the anterior chamber. Continued use of this type of intraocular lens can cause chronic uveitis, glaucoma, iris deformity and intraocular hemorrhage. This intraocular lens is only composed of the optical lens and the haptics. The haptics are positioned at the anterior chamber angle in order to stabilize the intraocular lens. But the angle and the iris near the angle are not as rigid and stable as the cornea or sclera for the fixation of an intraocular lens. The iris plane is like a curtain and can fluctuate easily. As a result, fixation of the intraocular lens in this area is quite difficult. Additionally, it is very difficult to measure the actual interangular diameter of the anterior chamber (the diameter from the anterior chamber angle at one point to the one at the opposite side) accurately. As such, it is very difficult to choose the proper diameter of the intraocular lens. If a smaller intraocular lens is chosen, then it may create a very loose intraocular lens fitting which can cause continuous rotation in the anterior chamber so as to result in chronic irritation of the intraocular structure. If a larger intraocular lens is chosen, the intraocular lens would push the iris near the angle so as to result in iris and pupil deformities.

U.S. Pat. No. 6,322,589, issued on Nov. 27, 2001 to J. S. Cumming, teaches an intraocular lens having fixated haptics. This intraocular lens is implanted within the natural capsular bags of human eyes. These lenses have features on the distal end portions so as to prevent movement or sliding thereof relative to fibrosis pockets or tunnels defined about proximally adjacent haptics portions in order to fixate the haptics against dislocation. Unfortunately, this type of intraocular lens will have the tendency to move or rotate in the capsular bag until capsular fibrosis develops. This intraocular lens is not supported, in any way, by the cornea or the sclera but is solely supported by the capsular bag.

It is an object of the present invention to overcome the above-stated problems encountered in the prior art and to provide an artificial intraocular lens that can be supported by the cornea.

It is another object of the present invention to provide an artificial intraocular lens which displays a desirable refraction index, can be firmly fixed to the cornea with few complications after surgical transplantation, and also allows the liquid of the anterior chamber to flow smoothly so as to prevent the endothelial cells of the cornea from being damaged.

It is a further object of the present invention to provide a fixation technique for such an intraocular lens which fixes the intraocular lens within the anterior chamber so as to decrease the likelihood of irritation of the iris, cataracts, glaucoma, chronic uveitis, hemorrhages, or distortion of the shape of the pupil.

It is another object of the present invention to provide a method and apparatus for installing an intraocular lens which allows the intraocular lens to be easily manipulated for angle adjustment, replacement, or refractive power accuracy.

It is another object of the present invention to provide a method and apparatus for installing an intraocular lens which provides for astigmatism correction.

It is another object of the present invention to provide a method and apparatus for securing an intraocular lens within the anterior chamber which facilitates the free convection of aqueous humor against the corneal endothelium so as to minimize potential damage thereto.

These and other objects and advantages of the present invention will become apparent from a reading of the attached specification and appended claims.

BRIEF SUMMARY OF THE INVENTION

The present invention is an apparatus for improving vision comprising an intraocular lens, haptics extending outwardly from the periphery of the intraocular lens, and a fixation means connected to the haptics. The fixation means serves to position the intraocular lens in the anterior chamber of the cornea. The fixation means is implanted into the cornea or into a sclera adjacent to the cornea.

In the preferred embodiment of the present invention, the intraocular lens is of an asymmetrical shape. In particular, the intraocular lens is a truncated circular lens with the truncation being formed along an upper edge thereof.

In the present invention, the haptics comprise a first element affixed to a first location on the periphery of the intraocular lens and extending radially outwardly therefrom, and a second element affixed to a second location on the periphery of the intraocular lens and extending radially outwardly therefrom. Each of the first and second elements can be releasably secured to the periphery of the intraocular lens.

In the present invention, the first anchor has a proximal end and a distal end with the first element secured to the proximal end of the first anchor. A second anchor also has a proximal end and a distal end with the second element secured to the proximal end of the second anchor. In one embodiment of the present invention, each of the first and second elements are releasably secured to the proximal ends of the respective first and second anchors. Each of the anchors has a generally L-shaped configuration. The proximal end of the anchor is connected to the haptics. The distal end of the anchor is implanted into the cornea or into the sclera. The distal end of the anchor has at least one hole formed therein. The proximal end of the anchor can have a receptacle formed therein for releasably securing the haptics thereto.

The present invention is also a method of installing an intraocular lens into a human eyeball comprising the steps of: (1) implanting a first anchor into a cornea or a sclera of the eyeball such that the first anchor has a proximal end extending into the anterior chamber of the eyeball; (2) implanting a second anchor into the cornea or the sclera such that the second anchor has a proximal end extending into the anterior chamber of the eyeball; (3) forming the intraocular lens so as to have haptics extending outwardly therefrom; (4) connecting the haptics to the first and second anchors such that the intraocular lens is positioned in the anterior chamber forward of an iris plane and a lens of the eyeball; and (5) positioning the haptics 34 to the artificial angle 11, formed by a proximal end of the first anchor 36 and the inner side of the cornea or sclera near the cornea, anterior to anchor 36.

DETAILED DESCRIPTION OF THE INVENTION

Figure 1:
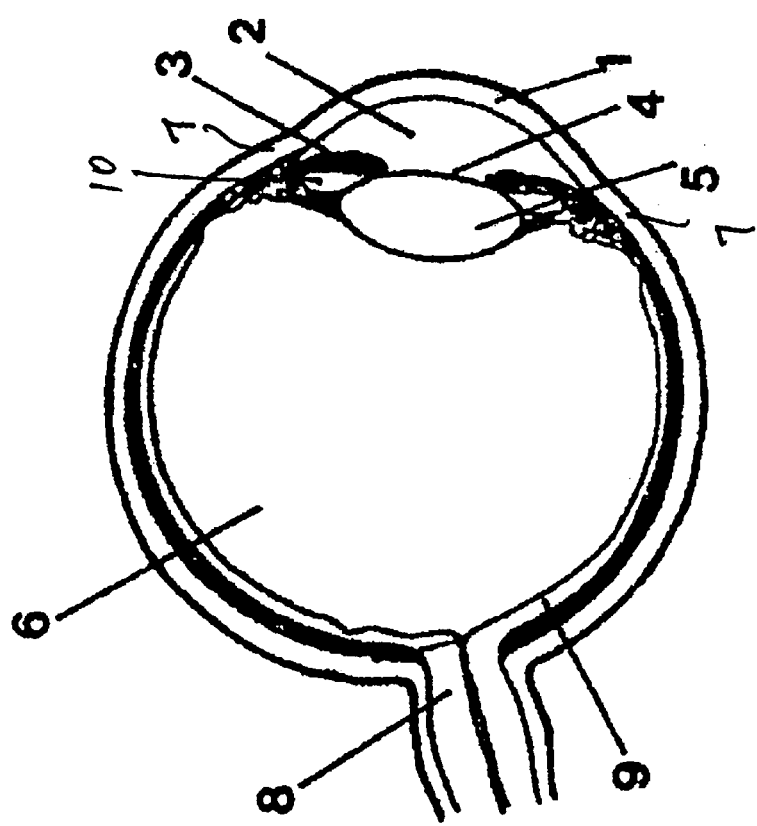
FIG. 1 is a cross-sectional view showing a conventional human eyeball.
Figure 2:
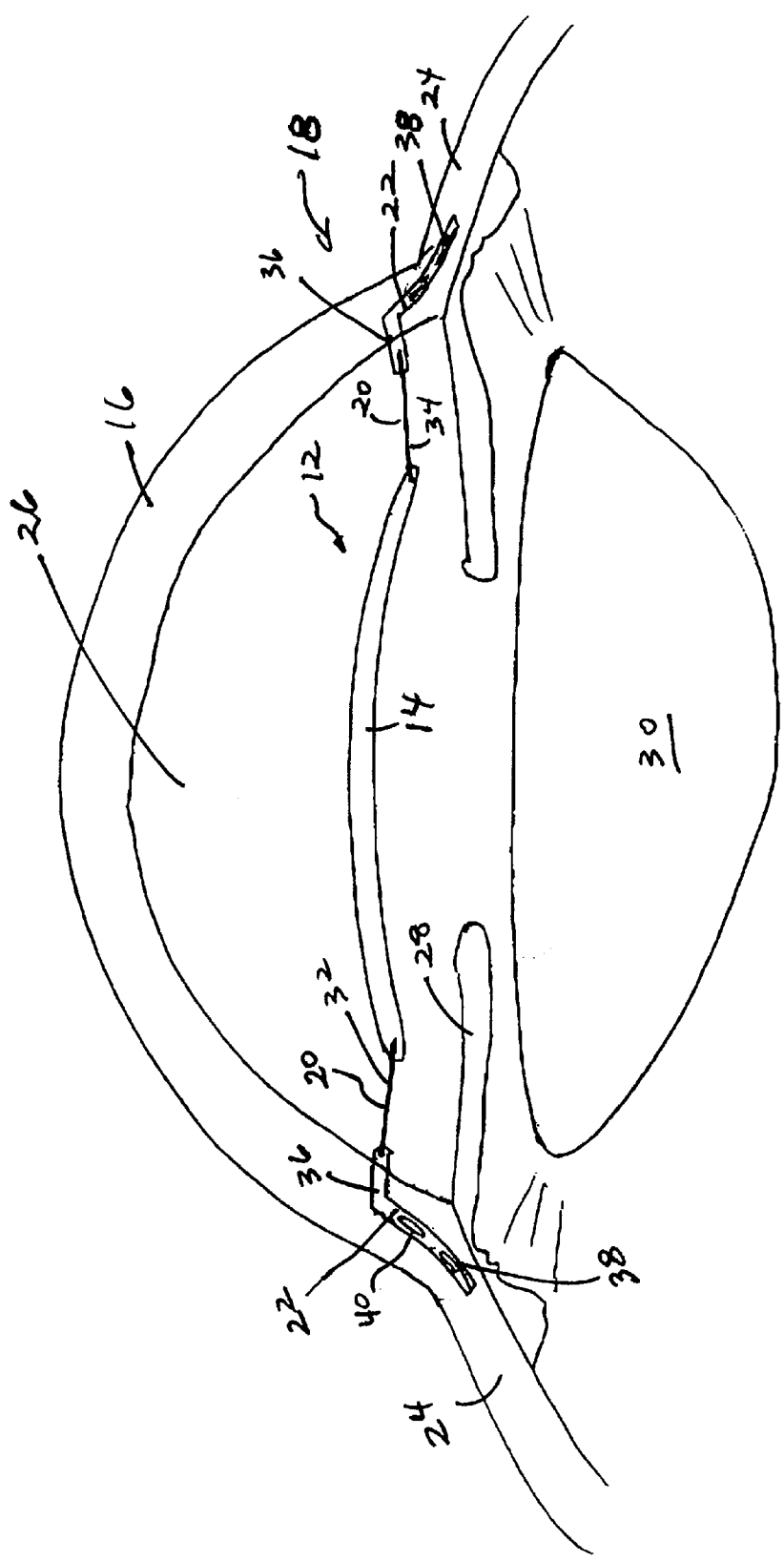
FIG. 2 is a diagrammatic illustration showing the securing of the intraocular lens in accordance with the teachings of the present invention within the cornea.

Referring to FIG. 2, there is shown the apparatus 12 of the present invention for the installation of an intraocular lens 14 within the cornea 16 of human eyeball 18. In particular, the apparatus 12 includes the intraocular lens 14, haptics 20 extending outwardly from a periphery of the intraocular lens 14 and a fixation means 22 connected to the haptics 20 and implanted within the cornea 16 or the sclera 24 of human eyeball 18. It can be seen that the intraocular lens 14 is positioned within the anterior chamber 26. The intraocular lens 14 is particularly positioned forward of and spaced from the iris plane 28 and forward of the lens 30.

As can be seen in FIG. 2, the intraocular lens 14 has a diameter suitable for extending across the opening in the iris plane 28. The haptics 20 include a first element 32 and a second element 34 extending outwardly of the periphery of the intraocular lens 14. Elements 32 and 34 can be in the nature of small wires, lines, or other extensible elements which can be affixed to the periphery of the intraocular lens 14 and in a position suitable for securement to the fixing means 22. The elements 32 and 34 should also be suitable for supporting the intraocular lens 14 in a desired position within the anterior chamber 26. In one form of the present invention, the elements 32 and 34 can be removably secured to the intraocular lens 14. In an alternative embodiment of the present invention, the opposite ends of the elements 32 and 34 can be removably secured to the fixation means 22.

Importantly, in the present invention, the fixation means 22 is a generally L-shaped member having a proximal end 36 and a distal end 38. The distal end 38 has a plurality of holes 40 formed therein. Holes 40 facilitate the ability to secure the anchor 36 within the cornea 16 or the sclera 24. The holes 40 will allow fibrous material to grow therethrough so as to rigidly secure the anchor 22 within the cornea 16 or the sclera 24. The proximal end 36 of each of the anchors 22 will extend outwardly through the inner wall of the cornea 16 and into the anterior chamber 26. It can be seen that the end of the first element 32 and the end of the second element 34 are secured within the proximal end 36 of the anchors 22. In this manner, the intraocular lens 14 can be supported in its desired position within the human eyeball 18.

Figure 3A:
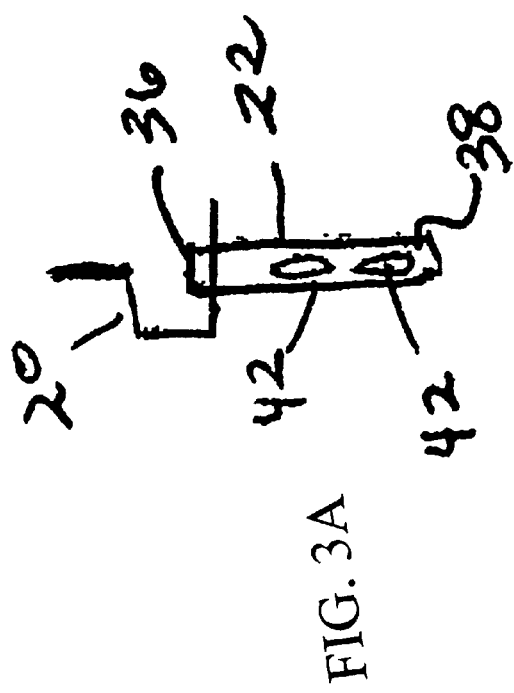
FIGS. 3A and 3B are, respectively, anterior and lateral views of one form of the anchor in accordance with the teachings of the present invention.
Figure 3B:
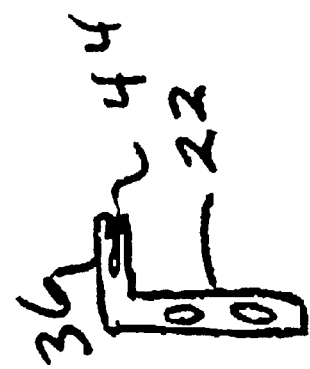

FIGS. 3A and 3B show one form of the anchor 22. It can be seen that anchor 22 has holes 42 formed in its distal end 38. The first element 20 is illustrated as secured within the proximal end 36 of the anchor 22. FIG. 3B shows that the anchor 22 has a generally L-shaped configuration. A slotted portion 44 is formed in the proximal end 36 so as to releasably secure the first element 32 therein.

Figure 4A:
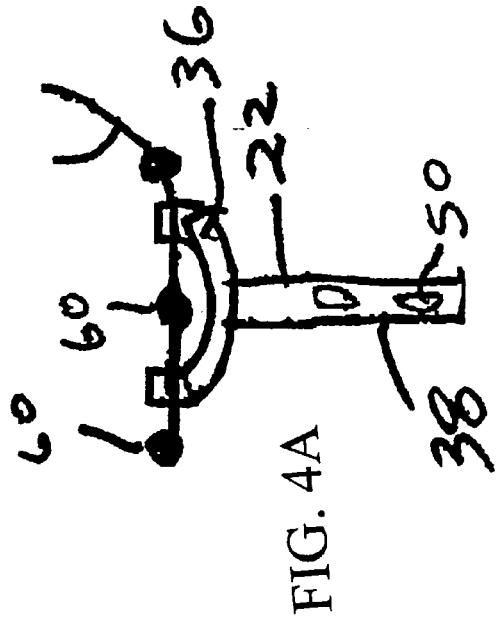
FIGS. 4A and 4B, respectively, show anterior and lateral view of an alternative form of the anchor in accordance with the teachings of the present invention.
Figure 4B:
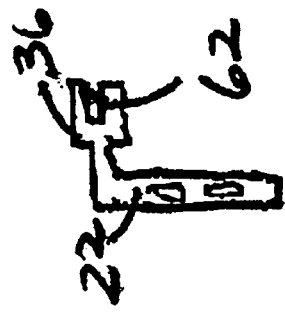

FIGS. 4A and 4B show an alternative embodiment of the anchor 22. In this alternative embodiment, the anchor 22 also has a generally L-shaped configuration (as shown in FIG. 4B). The distal end 38 of anchor 22 has a plurality of holes 50 formed therein. The proximal end 36 includes a pair of slotted members which are spaced away from each other. The proximal end 36 includes small clamps which can receive the end of the first element 32 therein. Small balls 60 are formed along the end of the first element 32 so as to allow for positive securement of the first element 32 within the small clamps of the anchor 22.

Figure 5:
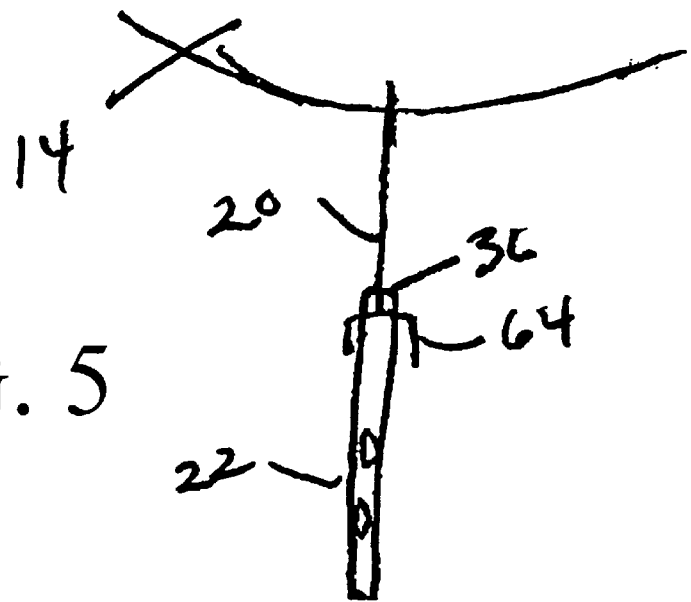
FIG. 5 is an anterior view showing a still further form of the anchor for securing the haptics thereto.

FIG. 5 shows a further alternative embodiment of the present invention in which the haptics 20 extends outwardly from the intraocular lens 14. The opposite end 64 of the haptics 20 is secured anterior to the proximal end 36 of anchor 22. The haptic 34 is positioned anterior to proximal end 36, at an angle formed by the inner side of the cornea or sclera near the cornea anterior to the anchors 22.

It should be noted with the present invention that the first element 32 and the second element 34 can be fixedly and permanently secured to the intraocular lens 14. However, and alternatively, the elements 32 and 34 can be permanently secured to the respective anchors 22 and joined to the periphery of the intraocular lens on a removable basis.

Figure 6:
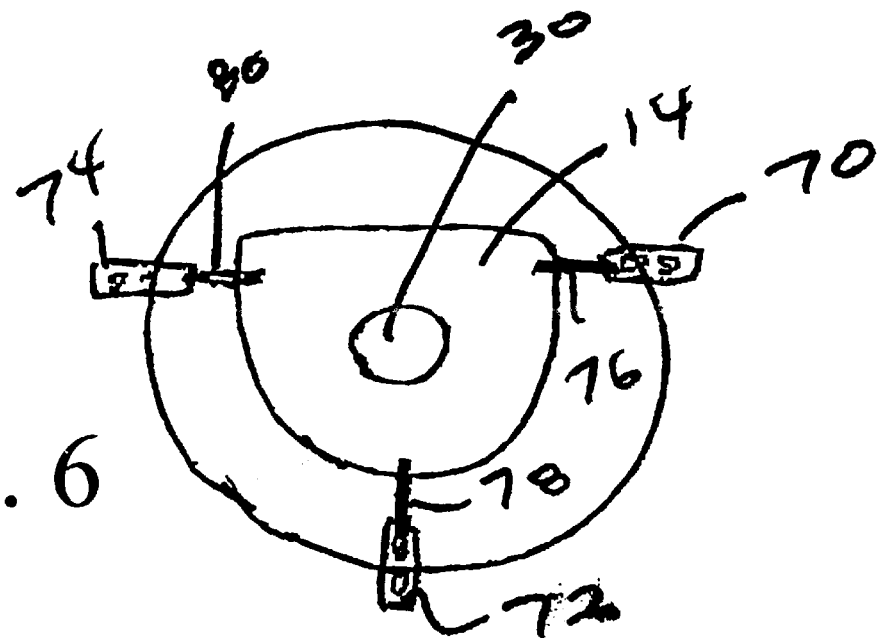
FIG. 6 is a forward view showing the shape of the intraocular lens and its securement over the lens and iris of a human eye.

FIG. 6 shows the intraocular lens 14 as secured over the crystalline lens 30 through the use of a plurality of anchor members 70, 72 and 74. Each of the anchor members 70, 72 and 74 has respective elements 76, 78 and 80 extending to the intraocular lens 14. Each of the anchors 70, 72 and 74 will be secured within the cornea or the sclera in the manner described herein previously. In FIG. 6, it can be seen that the intraocular lens 14 has a generally truncated circular configuration with the upper end of the circular configuration of intraocular lens 14 being truncated. It should be noted that, within the concept of the present invention, the intraocular lens can take on a wide variety of other asymmetrical configurations. The purpose of the asymmetrical configuration of the intraocular lens 14 is to promote convection of the aqueous humor through the posterior and anterior chambers of the eye. The lens 14 is specifically formed of a material that is either polymethylmethacrylate, acrylic or silicone.

Importantly, in the present invention, the fixation technique has a proximal end that allows for the exchanging of lenses 14 with either a reusable connector or a reusable supporter. There are many different types of fixation apparatus and reusable connector parts can be utilized in conjunction with the concept of the present invention.

The fixation apparatus of the present invention can provide a wide variety of major advantages. Most importantly, the present invention reduces the potential for complications. The fixation apparatus of the present invention will hold the intraocular lens 14 in the anterior chamber 26. Neither the lens 14 nor the fixation means 22 are in contact with the iris 28, the crystalline lens 30, or the anterior chamber angle. As a result of this lack of contact, there is a decrease in the likelihood of irritation of the iris, cataracts, glaucoma, chronic uveitis, hemorrhage or distortion in the shape of the pupil.

The intraocular lens of the present invention can be easily tilted so as to change the angle of the intraocular lens. This can be accomplished by simply changing the location of the anchors 22 within the cornea 16 or the sclera 24.

The intraocular lens is easily replaced as required due to refractive change. The haptics 20 can be dislocated from the anchors 22 via the reusable connector. Since the anchoring apparatus will remain in the cornea, it is only necessary to connect the haptics again to the anchoring apparatus. The intraocular lens 14 may then be removed from the anterior chamber 26 and replaced with a new intraocular lens which can be attached to the fixation means 22.

The fixation means 22 of the present invention is placed in a predictable anatomic position which allows for an accurate determination of the focal length. Other intraocular lens fixation methods are attached to anatomical structures with individual variations. It is relatively difficult to measure the distance from the apex of the cornea 16 to that of the anterior chamber angle, the iris plane 28 or to the crystalline lens surface 30. As a result, the other types of intraocular lens are very difficult to properly locate. These particular structures of the eye are not as stable as the cornea 16 or the sclera 24. The present invention utilizes such structures for the stable attachment of the intraocular lens. When the intraocular lens is secured to the cornea or to the sclera, the location of such intraocular lens 14 is stable and highly predictable since the intraocular lens can be installed in a planned location by adjusting the placement of the fixation means into the cornea 16. The distance from the apex to the fixation means is easily measured. The focal length is thus stable which can result in higher refractive accuracy.

In the present invention, the lens 14 does not rotate. As a result, it is possible to obtain accurate corrections of astigmatism. With the exception of the iris-supported intraocular lens, all of the other prior art intraocular lens fixation methods have a tendency towards lens rotation after implantation. As such, astigmatism correction is impractical. The treatment of astigmatism is achieved by the implantation of the intraocular lens 14 in accordance with the teachings of the present invention which is manufactured with an axis specific to the need for refraction. The custom correction of refractive error is made possible in the present invention through the use of a stable, predictable spatial position of the intraocular lens 14. As a result, the intraocular lens 14 of the present invention can be used to correct myopia, hyperopia, astigmatism and mixed refractive errors.

The intraocular lens of the present invention is relatively large in comparison with other intraocular lens types. As a result, the present invention can reduce glare, halos and degradation of night vision.

Importantly, the present invention facilitates the convection of aqueous humor in the chambers of the eyeball 18. There is normally aqueous humor convection current in the anterior chamber 26. Aqueous humor coming out of the posterior chamber 10 is warmer than the fluid in the anterior chamber 26. This aqueous humor moves until it meets the upper part of the anterior chamber angle and also meets the cooler cornea 16. Such humor then goes down following just behind the corneal endothelium. This is called convection current of aqueous humor. It plays a key role for providing oxygen and nutrients to the corneal endothelium. In this manner, the aqueous circulation keeps the corneal endothelium healthy.

The present invention enhances such circulation by truncating the intraocular lens 14 at the upper or superior position. The truncation will allow for the free convection of aqueous humor against the corneal endothelium so as to minimize potential damage thereto. The superior positioning of the truncation should also minimize glare due to partial covering of this position of the cornea by the ptosis of the upper eyelid.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

We claim:

1. An apparatus for improving vision comprising:
   an intraocular lens;
   haptics extending outwardly from a periphery of said intraocular lens; and
   a fixation means connected to said haptics, said fixation means for positioning said intraocular lens in said anterior chamber of a cornea, said fixation means for implanting into the cornea or into a sclera adjacent to the cornea, said fixation means being detachably connected or interconnected to said intraocular lens.

2. The apparatus of claim 1, said intraocular lens being of an asymmetrical shape.

3. The apparatus of claim 2, said intraocular lens being truncated along an upper edge thereof.

4. The apparatus of claim 1, said haptics comprising: a first element affixed to a first location on said periphery of said intraocular lens and extending radially outwardly therefrom; and a second element affixed to a second location on said periphery of said intraocular lens and extending radially outwardly therefrom.

5. The apparatus of claim 4, said first element being releasably secured to said periphery of said intraocular lens, said second element being releasably secured to said periphery of said intraocular lens.

6. The apparatus of claim 4, said fixation means comprising: a first anchor having a proximal end and a distal end, said first element being secured to said proximal end; and a second anchor having a proximal end and a distal end, said second element being secured to said proximal end of said second anchor.

7. The apparatus of claim 6, said first element being releasably secured to said proximal end of said first anchor, said second element being releasably secured to said proximal end of said second anchor.

8. An apparatus for improving vision comprising:
   an intraocular lens;
   haptics extending outwardly from opposite sides of a periphery of said intraocular lens; and
   a fixation means connected to said haptics, said fixation means for positioning said intraocular lens in said anterior chamber of a cornea, said fixation means for implanting into the cornea or into a sclera adjacent to the cornea, said fixation means comprising:
   a first anchor having a proximal end and a distal end, said haptics secured to said proximal end of said first anchor, said distal end of said first anchor suitable for external implantation into the cornea or the sclera; and
   a second anchor having a proximal end and a distal end, said haptics secured to said proximal end of said second anchor, said distal end of said anchor suitable for external implantation into the cornea or the sclera, each of said first and second anchors having a generally L-shaped configuration.

9. The apparatus of claim 8, said distal end of said anchor having at least one hole formed therein.

10. The apparatus of claim 8, said proximal end of said anchor having a receptacle formed therein, said receptacle being releasably secured to said haptics.

11. The apparatus of claim 8, said fixation means comprising an anchor formed of a material selected from the group consisting of polymethylmethacrylate, acrylic and silicone.

12. A method of installing an intraocular lens into a human eyeball comprising:
   implanting a first anchor into a cornea or a sclera of the eyeball such that the first anchor has a proximal end extending into an anterior chamber of the eyeball,
   implanting a second anchor into the cornea or the sclera such that the second anchor has a proximal end extending into the anterior chamber of the eyeball;
   forming the intraocular lens so as to have haptics extending outwardly therefrom; and
   connecting said haptics to said first and second anchors such that the intraocular lens is positioned in said anterior chamber forward of an iris plane and a lens of the eyeball, said step of connected occurring subsequent to said steps of implanting.

13. The method of claim 12, further comprising fonning each of said first and second anchors so as to have a generally L-shaped configurations, said steps of implanting comprising totally implanting a distal end of the anchor into the cornea or the sclera, said distal end having at least one hole formed therein, each of said first and second anchors being formed of a material selected from the group consisting of polymethylmethacrylate, acrylic and silicone.

14. The method of claim 12, further comprising:
   forming said intraocular lens so as to have a truncated circular shape.

* * * * *